United States Patent
Benderly et al.

(10) Patent No.: US 7,026,502 B2
(45) Date of Patent: Apr. 11, 2006

(54) PREPARATION OF UNSATURATED CARBOXYLIC ACIDS AND UNSATURATED CARBOXYLIC ACID ESTERS FROM ALKANES AND/OR ALKENES

(75) Inventors: Abraham Benderly, Elkins Park, PA (US); Anne Mae Gaffney, West Chester, PA (US)

(73) Assignee: Rohm and Haas Company, Philadelphia, PA (US)

( * ) Notice: Subject to any disclaimer, the term of this patent is extended or adjusted under 35 U.S.C. 154(b) by 324 days.

(21) Appl. No.: 10/681,420

(22) Filed: Oct. 7, 2003

(65) Prior Publication Data

US 2004/0077897 A1    Apr. 22, 2004

Related U.S. Application Data

(60) Provisional application No. 60/419,619, filed on Oct. 18, 2002.

(51) Int. Cl.
*C07C 67/00* (2006.01)
*C07C 51/16* (2006.01)

(52) U.S. Cl. ...................... 560/208; 562/549

(58) Field of Classification Search ............... None
See application file for complete search history.

(56) References Cited

U.S. PATENT DOCUMENTS

| 3,264,225 | A | | 8/1966 | Callahan et al. |
| 3,387,038 | A | | 6/1968 | Koch et al. |
| 3,819,685 | A | * | 6/1974 | Grasselli et al. ............ 560/208 |
| 4,060,545 | A | | 11/1977 | Miller et al. |
| 5,380,933 | A | | 1/1995 | Ushikubo et al. |
| 6,252,122 | B1 | * | 6/2001 | Tenten et al. ............... 568/475 |

FOREIGN PATENT DOCUMENTS

| EP | 0608838 A | 8/1994 |
| EP | 1193240 A | 4/2002 |
| EP | 1318127 A | 6/2003 |
| WO | WO0198246 A | 12/2001 |

OTHER PUBLICATIONS

Linde, V.R., et al: "Production of Methacrylic Acid Esters by the Heterogeneous Catalytic Oxidation of Alpha-Methacrolein in the Presence of Alcohols"; Petroleum Chemistry, vol. 34, No. 6, 1994, pp. 513-517, CP009024570.

* cited by examiner

*Primary Examiner*—Paul A. Zucker
(74) *Attorney, Agent, or Firm*—Marcella M. Bodner

(57) ABSTRACT

Unsaturated carboxylic acids (and esters thereof) are prepared directly from alkanes (and alcohols) utilizing vapor phase oxidative esterification.

12 Claims, No Drawings

PREPARATION OF UNSATURATED CARBOXYLIC ACIDS AND UNSATURATED CARBOXYLIC ACID ESTERS FROM ALKANES AND/OR ALKENES

CROSS REFERENCE TO RELATED PATENT APPLICATIONS

This is a non-provisional patent application of co-pending U.S. provisional patent application Ser. No. 60/419,619 filed Oct. 18, 2002.

The present invention is directed to the preparation of unsaturated carboxylic acids, such as acrylic or methacrylic acid, and esters of unsaturated carboxylic acids, such as esters of acrylic or methacrylic acid. More particularly, the present invention is directed to the preparation of unsaturated carboxylic acids or esters of unsaturated carboxylic acids by the catalytic oxidation of alkanes.

The direct oxidation of propylene or isobutylene to an aldehyde is well known in the art. See U.S. Pat. Nos. 3,264,225 and 3,387,038. The preparation of esters from unsaturated aldehydes and alcohols is also well known in the art. See U.S. Pat. No. 3,819,685. The preparation of esters of unsaturated acids by the oxidative esterification of propylene or isobutylene in a single fluidized bed reactor is also known. See U.S. Pat. No. 4,060,545.

However, a process for the oxidative esterification of an alkane to form an ester of an unsaturated carboxylic acid is not presently known. Such a process would advantageously benefit from the price differential between an alkene feedstock and an alkane feedstock. Moreover, by preparing the ester in a single step process and obtaining high yields, the cost of producing the ester is greatly reduced due to the elimination of one or more reactors.

Thus, in a first aspect, the present invention provides a process for the production of esters of unsaturated carboxylic acids, the process comprising:

passing a gaseous alkane, molecular oxygen and a gaseous alcohol to a reactor, the reactor containing one or more oxidation catalysts cumulatively effective for the oxidation of the alkane to an ester of its corresponding unsaturated carboxylic acid with the alcohol;

the reactor being operated at a temperature of from 500° C. to 1000° C., with a reactor residence time of no greater than 100 milliseconds.

As a first alternative, in a second aspect, the present invention provides a process for the production of esters of unsaturated carboxylic acids, the process comprising:

passing a first gaseous stream comprising an alkane and molecular oxygen to a reactor;

passing a second gaseous stream comprising an alcohol to the reactor;

the reactor containing one or more oxidation catalysts cumulatively effective for the oxidation of the alkane to an ester of its corresponding unsaturated carboxylic acid with the alcohol;

the one or more oxidation catalysts comprising a first catalyst effective for the oxidation of the alkane to its corresponding alkene and a second catalyst effective for the oxidation of the alkene, in the presence of the alcohol, to an ester of its corresponding unsaturated carboxylic acid with the alcohol;

the first catalyst being disposed in a first reaction zone;

the second catalyst being disposed in a second reaction zone;

the first reaction zone being disposed upstream of the second reaction zone relative to the direction of flow of the first gaseous stream through the reactor;

the second gaseous stream being fed to the reactor intermediate the first reaction zone and the second reaction zone;

the first reaction zone being operated at a temperature of from 500° C. to 1000° C., with a first reaction zone residence time of no greater than 100 milliseconds;

the second reaction zone being operated at a temperature of from 100° C. to 300° C., with a second reaction zone residence time of no greater than 100 milliseconds.

As a further alternative, in a third aspect, the present invention provides a process for the production of esters of unsaturated carboxylic acids, the process comprising:

passing a first gaseous stream comprising an alkane and molecular oxygen to a reactor;

passing a second gaseous stream comprising an alcohol to the reactor;

the reactor containing one or more oxidation catalysts cumulatively effective for the oxidation of the alkane to an ester of its corresponding unsaturated carboxylic acid with the alcohol;

the one or more oxidation catalysts comprising a first catalyst effective for the oxidation of the alkane to its corresponding unsaturated aldehyde and a second oxidation catalyst effective for the oxidation of the unsaturated aldehyde, in the presence of the alcohol, to an ester of its corresponding unsaturated carboxylic acid with the alcohol;

the first oxidation catalyst being disposed in a first reaction zone;

the second oxidation catalyst being disposed in a second reaction zone;

the first reaction zone being disposed upstream of the second reaction zone relative to the direction of flow of the first gaseous stream through the reactor;

the second gaseous stream being fed to the reactor intermediate the first reaction zone and the second reaction zone;

the first reaction zone being operated at a temperature of from 500° C. to 1000° C., with a first reaction zone residence time of no greater than 100 milliseconds;

the second reaction zone being operated at a temperature of from 100° C. to 300° C., with a second reaction zone residence time of no greater than 100 milliseconds.

As a yet further alternative, in a fourth aspect, the present invention provides a process for the production of esters of unsaturated carboxylic acids, the process comprising:

passing a first gaseous stream comprising an alkane and molecular oxygen to a reactor;

passing a second gaseous stream comprising an alcohol to the reactor;

the reactor containing one or more oxidation catalysts cumulatively effective for the oxidation of the alkane to an ester of its corresponding unsaturated carboxylic acid with the alcohol;

the one or more oxidation catalysts comprising a first catalyst effective for the oxidation of the alkane to its corresponding alkene, a second catalyst effective for the oxidation of the alkene to its corresponding unsaturated aldehyde, and a third catalyst effective for the oxidation of the unsaturated aldehyde, in the presence of the alcohol, to an ester of its corresponding unsaturated carboxylic acid with the alcohol;

the first catalyst being disposed in a first reaction zone;

the second catalyst being disposed in a second reaction zone;

the third catalyst being disposed in a third reaction zone;

the first reaction zone being disposed upstream of the second reaction zone relative to the direction of flow of the first gaseous stream through the reactor;

the second reaction zone being disposed upstream of the third reaction zone relative to the direction of flow of the first gaseous stream through the reactor;

the second gaseous stream being fed to the reactor intermediate the second reaction zone and the third reaction zone;

the first reaction zone being operated at a temperature of from 500° C. to 1000° C., with first reaction zone residence time of no greater than 100 milliseconds;

the second reaction zone being operated at a temperature of from 200° C. to 400° C., with a second reaction zone residence time of no greater than 100 milliseconds;

the third reaction zone being operated at a temperature of from 100° C. to 300° C., with a third reaction zone residence time of no greater than 100 milliseconds.

As a still further alternative, in a fifth aspect, the present invention provides a process for the production of esters of unsaturated carboxylic acids, the process comprising:

reacting an unsaturated aldehyde with an alcohol to form an acetal;

passing a gaseous stream comprising the so-formed acetal and molecular oxygen to a reactor, the reactor containing at least one catalyst effective for oxidation of an acetal to its corresponding ester;

the reactor being operated at a temperature of from 200° C. to 500° C., with a reactor residence time of no more than 100 milliseconds.

Commercially, the current process for acrylic acid manufacture involves a two-step catalytic oxidation reaction starting with a propene feed. In the first step, propene is converted to acrolein over a modified bismuth molybdate catalyst. In the second step, acrolein product from the first step is converted to acrylic acid using a catalyst composed of mainly molybdenum and vanadium oxides. In most cases, the catalyst formulations are proprietary to the catalyst supplier, but, the technology is well established. As previously noted, commercial incentives exist for using an alkane feedstock as compared to an alkene feedstock.

The direct oxidation of an alkane to its corresponding unsaturated carboxylic acid is known in the art. See U.S. Pat. No. 5,380,933. However, commercially viable yields have not yet been reported for such a process.

Thus, in a sixth aspect, the present invention provides a process for the production of unsaturated carboxylic acids, the process comprising:

passing a gaseous stream comprising an alkane and molecular oxygen to a reactor, the reactor containing one or more oxidation catalysts cumulatively effective for the oxidation of an alkane to its corresponding unsaturated carboxylic acid;

the reactor being operated at a temperature of from 500° C. to 1000° C., with a reactor residence time no greater than 100 milliseconds.

The invention can be advantageously utilized for the production of esters. Specifically, these esters include, but are not limited to, butyl acrylate from butyl alcohol and propane, β-hydroxyethyl acrylate from ethylene glycol and propane, methyl methacrylate from methanol and isobutane, butyl methacrylate from butyl alcohol and isobutane, and β-hydroxyethyl methacrylate from ethylene glycol and isobutane.

In addition to these esters, other esters may be formed through this invention by varying the type of alcohol introduced into the reactor and/or the -alkane introduced into the reactor.

Suitable alcohols include monohydric alcohols, dihydric alcohols and polyhydric alcohols. Of the monohydric alcohols reference may be made, without limitation, to $C_1$–$C_{20}$ alcohols, preferably $C_1$–$C_6$ alcohols, most preferably $C_1$–$C_4$ alcohols. The monohydric alcohols may be aromatic, aliphatic or alicyclic; straight or branched chain; saturated or unsaturated; and primary, secondary or tertiary. Particularly preferred monohydric alcohols include methyl alcohol, ethyl alcohol, propyl alcohol, isopropyl alcohol, butyl alcohol, isobutyl alcohol and tertiary butyl alcohol. Of the dihydric alcohols reference may be made, without limitation, to $C_2$–$C_6$ diols, preferably $C_2$–$C_4$ diols. The dihydric alcohols may be aliphatic or alicyclic; straight or branched chain; and primary, secondary or tertiary. Particularly preferred dihydric alcohols include ethylene glycol (1,2-ethanediol), propylene glycol (1,2-propanediol), trimethylene glycol (1,3-propanediol), 1,2-butanediol and 2,3-butanediol. Of the polyhydric alcohols reference will only be made to glycerol (1,2,3-propanetriol).

Suitable alkanes may have straight or branched chains and include $C_3$–$C_{25}$ alkanes, preferably $C_3$–$C_8$ alkanes such as propane, butane, isobutane, pentane, hexane and heptane. Particularly preferred are propane and isobutane.

In the present application, the terminology "cumulatively effective for the oxidation of an alkane to an ester of its corresponding unsaturated carboxylic acid with the alcohol" means that the catalyst(s) utilized will produce a product stream comprising an ester of the added alcohol with the unsaturated carboxylic acid corresponding to the added alkane when acting on a feed stream(s) comprising the alkane and the alcohol under the designated reaction conditions.

The unsaturated carboxylic acid corresponding to the added alkane is the α,β-unsaturated carboxylic acid having the same number of carbon atoms as the starting alkane and the same carbon chain structure as the starting alkane, e.g., acrylic acid is the unsaturated carboxylic acid corresponding to propane and methacrylic acid is the unsaturated carboxylic acid corresponding to isobutane.

Similarly, the unsaturated carboxylic acid corresponding to an alkene is the α,β-unsaturated carboxylic acid having the same number of carbon atoms as the alkene and the same carbon chain structure as the alkene, e.g., acrylic acid is the unsaturated carboxylic acid corresponding to propene and methacrylic acid is the unsaturated carboxylic acid corresponding to isobutene.

Likewise, the unsaturated carboxylic acid corresponding to an unsaturated aldehyde is the α,β-unsaturated carboxylic acid having the same number of carbon atoms as the unsaturated aldehyde and the same carbon chain structure as the unsaturated aldehyde, e.g., acrylic acid is the unsaturated carboxylic acid corresponding to acrolin and methacrylic acid is the unsaturated carboxylic acid corresponding to methacrolein.

The alkene corresponding to the added alkane is the alkene having the same number of carbon atoms as the starting alkane and the same carbon chain structure as the starting alkane, e.g., propene is the alkene corresponding to propane and isobutene is the alkene corresponding to isobutane. (For alkenes having four or more carbon atoms, the double bond is in the 2-position of the carbon-carbon chain of the alkene.)

The unsaturated aldehyde corresponding to the added alkane is the α,β-unsaturated aldehyde having the same number of carbon atoms as the starting alkane and the same carbon chain structure as the starting alkane, e.g., acrolein is the unsaturated aldehyde corresponding to propane and methacrolein is the unsaturated carboxylic acid corresponding to isobutane.

Similarly, the unsaturated aldehyde corresponding to an alkene is the α,β-unsaturated carboxylic acid having the same number of carbon atoms as the alkene and the same carbon chain structure as the alkene, e.g., acrolein is the unsaturated aldehyde corresponding to propene and methacrolein is the unsaturated aldehyde corresponding to isobutene.

With respect to the various groups of the Periodic Table of the Elements referenced hereinafter, the following definitions apply:

Group 1B comprises Cu, Ag and Au.
Group 3A comprises B, Al, Ga, In and Tl.
Group 3B comprises Sc, Y, La and Ac.
Group 4A comprises C, Si, Ge, Sn and Pb.
Group 4B comprises Ti, Zr and Hf.
Group 5A comprises N, P, As, Sb and Bi.
Group 5B comprises V, Nb and Ta.
Group 6B comprises Cr, Mo and W.
Group 7B comprises Mn, Tc and Re.
Group 8 comprises Fe, Ru, Os, Co, Rh, Ir, Ni, Pd and Pt.

In a first aspect of the invention, there is provided a process for the production of esters of unsaturated carboxylic acids, the process comprising: passing a gaseous alkane, molecular oxygen and a gaseous alcohol to a reactor, the reactor containing one or more oxidation catalysts cumulatively effective for the oxidation of the alkane to an ester of its corresponding unsaturated carboxylic acid with the alcohol; the reactor being operated at a temperature of from 500° C. to 1000° C., with a reactor residence time of no greater than 100 milliseconds.

Preferably, the process comprises contacting propane or isobutane, molecular oxygen and an alcohol with a catalyst at an elevated temperature. In addition, the feed may contain an adjuvant such as steam or a diluent such as an inert gas, e.g. nitrogen, argon or carbon dioxide.

Any source of molecular oxygen may be employed in this process, e.g. oxygen, oxygen-enriched gases or air. Air may be the most economical source of oxygen, especially in the absence of any recycle.

The alcohol may be added to the gaseous stream of alkane and molecular oxygen before entering the reactor, or it may be separately introduced into the reactor, e.g., at a point downstream from the point at which the alkane and molecular oxygen enter the reactor.

In a preferred embodiment of this first aspect of the invention, the catalyst may comprise a mixed metal oxide having the empirical formula

$$Mo_aV_bM_cN_dQ_eX_fO_g$$

wherein

M is an element selected from the group consisting of Te and Sb,

N is at least one element selected from the group consisting of Nb, Ta, W,

Ti, Al, Zr, Cr, Mn, B, In, As, Ge, Sn, Li, Na, K, Rb, Cs, Fr, Be, Mg, Ca, Sr, Ba, Hf and P, Q is at least one element selected from Group 8 of the periodic table of the elements, X is at least one element selected from the group consisting of Pb and Bi, a, b, c, d, e, f and g represent relative atomic amounts of the elements, and when a=1, b=0.01 to 1.0, c=0.01 to 1.0, d=0.01 to 1.0, e=0.001 to 0.1, f=0.001 to 0.1 and g depends on the oxidation state of the elements other than oxygen.

In a second aspect of the invention, there is provided a process for the production of esters of unsaturated carboxylic acids, the process comprising: passing a first gaseous stream comprising an alkane and molecular oxygen to a reactor; passing a second gaseous stream comprising an alcohol to the reactor; the reactor containing one or more oxidation catalysts cumulatively effective for the oxidation of the alkane to an ester of its corresponding unsaturated carboxylic acid with the alcohol; the one or more oxidation catalysts comprising a first catalyst effective for the oxidation of the alkane to its corresponding alkene and a second catalyst effective for the oxidation of the alkene, in the presence of the alcohol, to an ester of its corresponding unsaturated carboxylic acid with the alcohol; the first catalyst being disposed in a first reaction zone; the second catalyst being disposed in a second reaction zone; the first reaction zone being disposed upstream of the second reaction zone relative to the direction of flow of the first gaseous stream through the reactor; the second gaseous stream being fed to the reactor intermediate the first reaction zone and the second reaction zone; the first reaction zone being operated at a temperature of from 500° C. to 900° C., with a first reaction zone residence time of no greater than 100 milliseconds; the second reaction zone being operated at a temperature of from 100° C. to 300° C., with a second reaction zone residence time of no greater than 100 milliseconds.

In this second aspect of the invention, it is preferred to pass a first gaseous stream comprising propane or isobutane and molecular oxygen to the reactor; and to separately pass a second gaseous stream comprising the alcohol to the reactor. In addition, the feed may contain an adjuvant such as steam or a diluent such as an inert gas, e.g., nitrogen, argon or carbon dioxide.

Any source of molecular oxygen may be employed in this process, e.g., oxygen, oxygen-enriched gases or air. Air may be the most economical source of oxygen, especially in the absence of any recycle.

The first catalyst component may comprise a reducible metal oxide promoted with a metal selected from Group 8 of the periodic table of the elements supported on a three-dimensional support structure.

The support structure is three-dimensional, i.e. has dimensions along the x, y and z orthogonal axes of a Cartesian coordinate system, and affords a relatively high surface area per unit volume. Though lower and higher amounts are possible, in one embodiment, the support structure exhibits a surface area of 0.01 to 50 m²/g, preferably 0.1 to 10 m²/g.

Preferably, the support structure will have a porous structure and exhibit a pore volume percent ranging from 1 to 95%, more preferably 5 to 80%, and still more preferably 10 to 50%. Thus, the support structure permits relatively high feed velocities with insubstantial pressure drop.

Further, the support structure is sufficiently strong so that it does not fracture under the weight of the catalyst, which can range up to almost 100% of the weight of the combination of the catalyst and the support structure. More preferably, however, the support structure is at least 60% of the weight of the combination. Still more preferably, it is 70 to 99.99% of the weight of the combination. Even still more preferably, the support structure is 90 to 99.9% of the weight of the combination.

The exact physical form of the support structure is not particularly important so long as it meets the above noted general criteria. Examples of suitable physical forms include foam, honeycomb, lattice, mesh, monolith, woven fiber, non-woven fiber, gauze, perforated substrates (e.g., foil), particle compacts, fibrous mat and mixtures thereof For these supports it will be appreciated that typically one or more open cells will be included in the structure. The cell size may vary as desired, as may the cell density, cell surface area, open frontal area and other corresponding dimensions. By way of example, one such structure has an open frontal area of at least 75%. The cell shape may also vary and may include polygonal shapes, circles, ellipses, as well as others.

The support structure may be fabricated from a material that is inert to the reaction environment of the catalytic reaction. Suitable materials include ceramics such as silica, alumina, silica-alumina, aluminosilicate, zirconia, titania, boria, mullite, lithium aluminum silicate, oxide-bonded silicon carbide or mixtures thereof. (Alternatively, the catalyst may be prepared so as to define the support structure itself, e.g., by "green" compacting or another suitable technique.)

The catalysts may be applied to the support structure using any suitable art-disclosed technique. For instance, the catalyst may be vapor deposited (e.g., by sputtering, plasma deposition or some other form of vapor deposition). The catalyst may be coated thereon (e.g., by wash coating a support with a solution, slurry, suspension or dispersion of catalyst). The support may be coated with a catalyst powder (i.e. powder coating). (Alternatively, where the support structure is the catalyst itself, a "green" body of catalyst may be compacted to yield the desired structure.)

The catalyst may be a binary, ternary, quaternary or higher order compound. The reducible metal oxide may be an oxide of a metal selected from the group consisting of Cu, Cr, V, Mn, Nb, Mo, W, Re, Ga, Ge, In Sn, Sb, Tl, Pb, Bi, Te, As, Se, Zn, Y, Zr, Ta, Ce, Pr, Nd, Pm, Sm, Eu, Gd, Tb, Dy, Ho, Er, Tm, Yb, Lu and mixtures thereof Preferably, the reducible metal oxide is selected from the group consisting of Cu, Cr, V, Mn, Zn and mixtures thereof. The promoter is a metal from Group 8 of the periodic table of the elements (Fe, Ru, Os, Co, Rh, Ir, Ni, Pd and Pt), preferably a metal selected from the group consisting of Pt, Pd, Rh, Ir, Ru and mixtures thereof The promoter may preferably be present in an amount of from 0.0001 to 10 wt % of the catalyst composition (promoter plus reducible metal oxide), more preferably from 0.001 to 5 wt % of the catalyst composition, and still more preferably from 0.01 to 2 wt % of the catalyst composition.

Alternatively, the first catalyst may comprise platinum and tin supported on a three-dimensional structure (as previously described).

As a further alternative, the first catalyst may comprise platinum, rhodium and tin and/or tin oxides.

The second catalyst component may comprise:
(A) a catalyst comprising a mixed metal oxide having the empirical formula $Mo_aV_bM_cN_dO_e$ wherein
M is selected from the group consisting of Te and Sb,
N is at least one element selected from the group consisting of Nb, Ta, W, Ti, Al, Zr, Cr, Mn, B, In, As, Ge, Sn, Li, Na, K, Rb, Cs, Fr, Be, Mg, Ca, Sr, Ba, Hf and P, a, b, c, d and e represent relative atomic amounts of the elements, and
hen a=1, b=0.01 to 1.0, c=0.01 to 1.0, d=0.01 to 1.0 and e depends on the oxidation state of the elements other than oxygen; or
(B) a catalyst comprising a mixed metal oxide having the empirical formula $Mo_aSb_bO_c$ wherein
a, b and c represent relative atomic amounts of the elements, and when a=1, b=0.01 to 1.0 and c depends on the oxidation state of the elements other than oxygen; or
(C) a catalyst comprising a mixed metal oxide having the empirical formula $Mo_aSb_bBi_cO_d$ wherein
a, b, c and d represent relative atomic amounts of the elements, and when a=1, b=0.01 to 1.0, c=0.01 to 1.0 and d depends on the oxidation state of the elements other than oxygen.

Alternatively, the second catalyst may comprise:
(a) a supported catalyst comprising at least one element selected from the group consisting of Groups 5B, 6B, 7B, and 8 of the periodic table of the elements promoted with at least one element selected from Group 1B of the periodic table of the elements plus bismuth oxide acetate; or
(b) a catalyst comprising ruthenium; or
(c) a catalyst comprising Pd and Bi on a support; or
(d) a supported catalyst comprising Pd and at least one element selected from the group consisting of elements of Groups 3A, 4A, 5A and 6B of the periodic table of the elements and at least one element selected from the group consisting of elements of Groups 3B and 4B of the periodic table of the elements; or
(e) a supported catalyst comprising Pd and at least one element of Group 1B of the periodic table of the elements; or
(f) a supported catalyst comprising Pd and Pb; or
(g) a supported catalyst comprising Pd and at least one element selected from the group consisting of Ba, Au, La, Nb, Ce, Zn, Pb, Ca, Sb, K, Cd, V and Te.

In a third aspect of the invention, there is provided a process for the production of esters of unsaturated carboxylic acids, the process comprising: passing a first gaseous stream comprising an alkane and molecular oxygen to a reactor; passing a second gaseous stream comprising an alcohol to the reactor; the reactor containing one or more oxidation catalysts cumulatively effective for the oxidation of the alkane to an ester of its corresponding unsaturated carboxylic acid with the alcohol; the one or more oxidation catalysts comprise a first catalyst effective for the oxidation of the alkane to its corresponding unsaturated aldehyde and a second oxidation catalyst effective for the oxidation of the unsaturated aldehyde, in the presence of the alcohol, to an ester of its corresponding unsaturated carboxylic acid with the alcohol; the first catalyst being disposed in a first reaction zone; the second catalyst being disposed in a second reaction zone; the first reaction zone being disposed upstream of the second reaction zone relative to the direction of flow of the first gaseous stream through said reactor; the second gaseous stream being fed to the reactor intermediate the first reaction zone and the second reaction zone; the first reaction zone being operated at a temperature of from 500° C. to 900° C., with a first reaction zone residence time of no greater than 100 milliseconds; the second reaction zone being operated at a temperature of from 100° C. to 300° C., with a second reaction zone residence time of no greater than 100 milliseconds.

In this third aspect of the invention, it is preferred to pass a first gaseous stream comprising propane or isobutane and molecular oxygen to the reactor; and to separately pass a second gaseous stream comprising the alcohol to the reactor. In addition, the feed may contain an adjuvant such as steam or a diluent such as an inert gas, e.g., nitrogen, argon or carbon dioxide.

Any source of molecular oxygen may be employed in this process, e.g., oxygen, oxygen-enriched gases or air. Air may be the most economical source of oxygen, especially in the absence of any recycle.

The first catalyst may comprise a phosphate catalyst containing Mo, V, Nb and/or Ta. (See Japanese Laid-Open Patent Application Publication No.06-199731 A2.)

Alternatively, the first catalyst may comprise a mixed metal oxide having the formula $P_aMo_bV_cBi_dX_eY_fZ_gO_h$, wherein X is As, Sb, Si, B, Ge or Te; Y is K, Cs, Rb, or Tl; Z is Cr, Mn, Fe, Co, Ni, Cu, Al, Ga, In, Sn, Zn, Ce, Y or W; a, b, c, d, e, f, g and h are the relative atomic amounts of the elements; and, when b=12, $0<a\leq3$, c=0–3, $0<d\leq3$, $0<e\leq3$, f=0–3, g=0–3, and h depends on the oxidation state of the other elements. (See Japanese Laid-Open Patent application Publication No. 09-020700 A2.)

The second catalyst may comprise a superacid. A superacid, according to the definition of Gillespie, is an acid that is stronger than 100% sulfuric acid, i.e. it has a Hammett acidity value $H_0<-12$. Representative superacids include, but are not limited to: zeolite supported $TiO_2/(SO_4)_2$, $(SO_4)_2/ZrO_2$—$TiO_2$, $(SO_4)_2/ZrO_2$—$Dy_2O_3$, $(SO_4)_2/TiO_2$, $(SO_4)_2/ZrO_2$—NiO, $SO_4/ZrO_2$, $SO_4/ZrO_2$-$Al_2O_3$, $(SO_4)_2/Fe_2O_3$, $(SO_4)_2/ZrO_2$, $C_4F_9SO_3H$—$SbF_5$, $CF_3SO_3H$—$SbF_5$, Pt/sulfated zirconium oxide, $HSO_3F$—$SO_2ClF$, $SbF_5$—$HSO_3F$—$SO_2ClF$, $MF_5/AlF_3$ (M=Ta, Nb, Sb), $B(OSO_2CF_3)_3$, $B(OSO_2CF_3)_3$—$CF_3SO_3H$, $SbF_5$—$SiO_2$—$Al_2O_3$, $SbF_5$—$TiO_2$—$SiO_2$ and $SbF_5$—$TiO_2$. Preferably, solid superacids are utilized, e.g., sulfated oxides, supported Lewis acids and supported liquid superacids. Only a small number of oxides produce superacid sites on sulfation, including $ZrO_2$, $TiO_2$, $HfO_2$, $Fe_2O_3$ and $SnO_2$. The acid sites are generated by treating an amorphous oxyhydrate of these elements with $H_2SO_4$ or $(NH_4)_2SO_4$ and calcining the products at temperatures of 500° C.–650° C. During the calcination, the oxides are transformed into a crystalline tetragonal phase, which is covered by a small number of sulfate groups. $H_2MoO_4$ or $H_2WO_4$ may also be used to activate the oxide.

In the fourth aspect of this invention, there is provided a process for the production of esters of unsaturated carboxylic acids, the process comprising: passing a first gaseous stream comprising an alkane and molecular oxygen to a reactor; passing a second gaseous stream comprising an alcohol to the reactor; the reactor containing one or more oxidation catalysts cumulatively effective for the oxidation of the alkane to an ester of its corresponding unsaturated carboxylic acid with the alcohol; the one or more oxidation catalysts comprising a first catalyst effective for the oxidation of the alkane to its corresponding alkene, a second catalyst effective for the oxidation of the alkene to its corresponding unsaturated aldehyde, and a third catalyst effective for the oxidation of the unsaturated aldehyde, in the presence of the alcohol, to an ester of its corresponding unsaturated carboxylic acid with the alcohol; the first catalyst being disposed in a first reaction zone; the second catalyst being disposed in a second reaction zone; the third catalyst being disposed in a third reaction zone; the first reaction zone being disposed upstream of the second reaction zone relative to the direction of flow of the first gaseous stream through the reactor; the second reaction zone being disposed upstream of the third reaction zone relative to the direction of flow of the first gaseous stream through the reactor; the second gaseous stream being fed to the reactor intermediate the second reaction zone and the third reaction zone; the first reaction zone being operated at a temperature of from 500° C. to 900° C., with a first reaction zone residence time of no greater than 100 milliseconds; the second reaction zone being operated at a temperature of from 200° C. to 400° C., with a second reaction zone residence time of no greater than 100 milliseconds; the third reaction zone being operated at a temperature of from 100° C. to 300° C., with a third reaction zone residence time of no greater than 100 milliseconds.

In this fourth aspect of the invention, it is preferred to pass a first gaseous stream comprising propane or isobutane and molecular oxygen to the reactor; and to separately pass a second gaseous stream comprising the alcohol to the reactor. In addition, the feed may contain an adjuvant such as steam or a diluent such as an inert gas, e.g., nitrogen, argon or carbon dioxide.

Any source of molecular oxygen may be employed in this process, e.g., oxygen, oxygen-enriched gases or air. Air may be the most economical source of oxygen, especially in the absence of any recycle.

The first catalyst component may comprise a reducible metal oxide promoted with a metal selected from Group 8 of the periodic table of the elements supported on a three-dimensional support structure.

The support structure is three-dimensional, i.e. has dimensions along the x, y and z orthogonal axes of a Cartesian coordinate system, and affords a relatively high surface area per unit volume. Though lower and higher amounts are possible, in one embodiment, the support structure exhibits a surface area of 0.01 to 50 $m^2/g$, preferably 0.1 to 10 $m^2/g$.

Preferably, the support structure will have a porous structure and exhibit a pore volume percent ranging from 1 to 95%, more preferably 5 to 80%, and still more preferably 10 to 50%. Thus, the support structure permits relatively high feed velocities with insubstantial pressure drop.

Further, the support structure is sufficiently strong so that it does not fracture under the weight of the catalyst, which can range up to almost 100% of the weight of the combination of the catalyst and the support structure. More preferably, however, the support structure is at least 60% of the weight of the combination. Still more preferably, it is 70 to 99.99% of the weight of the combination. Even still more preferably, the support structure is 90 to 99.9% of the weight of the combination.

The exact physical form of the support structure is not particularly important so long as it meets the above noted general criteria. Examples of suitable physical forms include foam, honeycomb, lattice, mesh, monolith, woven fiber, non-woven fiber, gauze, perforated substrates (e.g., foil), particle compacts, fibrous mat and mixtures thereof For these supports it will be appreciated that typically one or more open cells will be included in the structure. The cell size may vary as desired, as may the cell density, cell surface area, open frontal area and other corresponding dimensions. By way of example, one such structure has an open frontal area of at least 75%. The cell shape may also vary and may include polygonal shapes, circles, ellipses, as well as others.

The support structure may be fabricated from a material that is inert to the reaction environment of the catalytic reaction. Suitable materials include ceramics such as silica, alumina, silica-alumina, aluminosilicate, zirconia, titania, boria, mullite, lithium aluminum silicate, oxide-bonded silicon carbide or mixtures thereof. (Alternatively, the catalyst may be prepared so as to define the support structure itself, e.g., by "green" compacting or another suitable technique.)

The catalysts may be applied to the support structure using any suitable art-disclosed technique. For instance, the catalyst may be vapor deposited (e.g., by sputtering, plasma deposition or some other form of vapor deposition). The catalyst may be coated thereon (e.g., by wash coating a support with a solution, slurry, suspension or dispersion of catalyst). The support may be coated with a catalyst powder (i.e. powder coating). (Alternatively, where the support structure is the catalyst itself, a "green" body of catalyst may be compacted to yield the desired structure.)

The catalyst may be a binary, ternary, quaternary or higher order compound. The reducible metal oxide may be an oxide of a metal selected from the group consisting of Cu, Cr, V, Mn, Nb, Mo, W, Re, Ga, Ge, In, Sn, Sb, Tl, Pb, Bi, Te, As, Se, Zn, Y, Zr, Ta, Ce, Pr, Nd, Pm, Sm, Eu, Gd, Tb, Dy, Ho, Er, Tm, Yb, Lu and mixtures thereof. Preferably, the reducible metal oxide is selected from the group consisting of Cu, Cr, V, Mn, Zn and mixtures thereof The promoter is a metal from Group 8 of the periodic table of the elements (Fe, Ru, Os, Co, Rh, Ir, Ni, Pd and Pt), preferably a metal selected from the group consisting of Pt, Pd, Rh, Ir, Ru and mixtures thereof. The promoter may preferably be present in an amount of from 0.0001 to 10 wt % of the catalyst composition (promoter plus reducible metal oxide), more preferably from 0.001 to 5 wt % of the catalyst composition, and still more preferably from 0.01 to 2 wt % of the catalyst composition.

Alternatively, the first catalyst may comprise platinum and tin supported on a three-dimensional structure (as previously described).

As a further alternative, the first catalyst may comprise platinum, rhodium and tin and/or tin oxides.

The second catalyst may comprise any of the well-known molybdenum, bismuth, iron-based mixed metal oxides such as those disclosed in U.S. Pat. Nos. 3,825,600; 3,649,930 and 4,339,355. For example, there may be used a mixed metal oxide of the formula

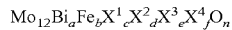

where
X$^1$ is nickel or cobalt,
X$^2$ is thallium, an alkali metal or an alkaline earth metal,
X$^3$ is phosphorus, arsenic, boron, antimony, tin, cerium, lead, niobium or tungsten,
X$^4$ is silicon, aluminum, titanium or zirconium,
a through f and n represent atomic ratios of the respective elements, and
a is from 0.5 to 5.0,
b is from 0.01 to 3.0,
c is from 3.0 to 10.0
d is from 0.02 to 2.0,
e is from 0 to 5.0,
f is from 0 to 10, and
n is determined by the valency and content of the elements other than oxygen;

or a mixed metal oxide of the formula

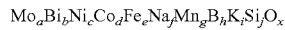

where a through j and x represent atomic ratios of the respective elements, and
when a is 12,
b is from 4 to 7,
c is from 0.05 to 5,
d is from 0.05 to 5,
e is from 0.05 to 2,
f is from 0 to 1,
g is from 0 to 1,
f+g is from 0.01 to 1,
h is from 0.02 to 2,
i is from 0 to 1,
j is from 6 to 48, and
x is a number satisfying the valency of the elements other than oxygen.

The third catalyst may comprise a superacid. A superacid, according to the definition of Gillespie, is an acid that is stronger than 100% sulfuric acid, i.e. it has a Hammett acidity value $H_0 < -12$. Representative superacids include, but are not limited to: zeolite supported $TiO_2/(SO_4)_2$, $(SO_4)_2/ZrO_2$—$TiO_2$, $(SO_4)_2/ZrO_2$—$Dy_2O_3$, $(SO_4)_2/TiO_2$, $(SO_4)_2/ZrO_2$—$NiO$, $SO_4/ZrO_2$, $SO_4/ZrO_2 Al_2O_3$, $(SO_4)_2/Fe_2O_3$, $(SO_4)_2/ZrO_2$, $C_4F_9SO_3H$—$SbF_5$, $CF_3SO_3H$—$SbF_5$, Pt/sulfated zirconium oxide, $HSO_3F$—$SO_2ClF$, $SbF_5$—$HSO_3FSO$—$SO_2ClF$, $MF_5/AlF_3$ (M=Ta, Nb, Sb), $B(OSO_2CF_3)_3$, $B(OSO_2CF_3)_3$—$CF_3SO_3H$, $SbF_5$—$SiO_2$—$Al_2O_3$, $SbF_5$—$TiO_2$—$SiO_2$ and $SbF_5$—$TiO_2$. Preferably, solid superacids are utilized, e.g., sulfated oxides, supported Lewis acids and supported liquid superacids. Only a small number of oxides produce superacid sites on sulfation, including $ZrO_2$, $TiO_2$, $HfO_2$, $Fe_2O_3$ and $SnO_2$. The acid sites are generated by treating an amorphous oxyhydrate of these elements with $H_2SO_4$ or $(NH_4)_2SO_4$ and calcining the products at temperatures of 500° C.–650° C. During the calcination, the oxides are transformed into a crystalline tetragonal phase, which is covered by a small number of sulfate groups. $H_2MoO_4$ or $H_2WO_4$ may also be used to activate the oxide.

In a fifth aspect of the invention, there is provided a process for the production of esters of unsaturated carboxylic acids, the process comprising: reacting an unsaturated aldehyde with an alcohol to form an acetal; passing a gaseous stream comprising the so-formed acetal and molecular oxygen to a reactor; the reactor containing at least one catalyst effective for the oxidation of the acetal to its corresponding ester; the reactor being operated at a temperature of from 200° C. to 500° C., with reactor residence time of no greater than 100 milliseconds.

Broadly, in this fifth aspect of the present invention, an alcohol is reacted with an unsaturated aldehyde to form an acetal. Such reaction can be carried out by contacting the aldehyde with an excess of the anhydrous alcohol in the presence of a small amount of an anhydrous acid, e.g., anhydrous HCl. Preferably, the aldehyde and the alcohol can be passed through a bed containing an acid catalyst, e.g., through a bed of a strongly acidic ion exchange resin, such as Amberlyst 15.

The so-formed acetal and molecular oxygen are fed to a reactor containing at least one catalyst effective for the oxidation of the acetal to its corresponding ester. Examples of such a catalyst include Pd and Bi on alumina or V oxides.

In this fifth aspect of the invention, any source of molecular oxygen may be employed in this process, e.g., oxygen, oxygen-enriched gases or air. Air may be the most economical source of oxygen, especially in the absence of any recycle.

In one embodiment of this fifth aspect of the invention, the unsaturated aldehyde is formed by oxidation of an alkane to its corresponding unsaturated aldehyde. This oxidation may be effected as a vapor phase oxidation of the alkane in the presence of a catalyst such as Pd and Bi on alumina or V oxides.

In a sixth aspect of the invention, there is provided a process for the production of unsaturated carboxylic acids, the process comprising: passing a gaseous stream comprising an alkane and molecular oxygen to a reactor, the rector containing one or more oxidation catalysts cumulatively effective for the oxidation of the alkane to its corresponding unsaturated carboxylic acid; the reactor being operated at a temperature of from 600° C. to 1000° C., with a reactor residence time of no greater than 100 milliseconds.

Broadly, in this sixth aspect of the present invention, an alkane is oxidized in a vapor phase catalytic oxidation with molecular oxygen in the presence of a catalyst such as a mixed metal oxide of the formula $Mo_aV_bTe_cX_dO_e$ (wherein X is at least one element selected from the group consisting of Nb, Ta, W, Ti, Al, Zr, Cr, Mn, Fe, Ru, Co, Rh, Ni, Pd, Pt, Sb, Bi, B, In and Ce; a, b, c and d are the mole fractions of the various elements exclusive of oxygen; e depends on the valence state of the other elements; and $0.25 < a < 0.98$, $0.003 < b < 0.5$, $0.003 < c < 0.5$ and $0.003 < d < 0.5$) or a mixed metal oxide containing Mo, V, Sb and A (wherein A is at least one element selected from the group consisting of Nb, Ta, Sn, W, Ti, Ni, Fe, Cr and Co) in the proportions represented by the empirical formula $MoV_iSb_jA_k$ (wherein each of i, j and k is from 0.001 to 3.0) in a reactor operated at a temperature of from 600° C. to 1000° C., with a reactor residence time no greater than 100 milliseconds.

In this sixth aspect of the invention, it is preferred to pass a gaseous stream comprising propane or isobutane and molecular oxygen to the reactor. In addition, the feed may contain an adjuvant such as steam or a diluent such as an inert gas, e.g., nitrogen, argon or carbon dioxide.

Any source of molecular oxygen may be employed in this process, e.g., oxygen, oxygen-enriched gases or air. Air may be the most economical source of oxygen, especially in the absence of any recycle.

The various mixed metal oxides of the present invention, as noted above, may be prepared in the following manner.

In a first step, a slurry or solution may be formed by admixing metal compounds, preferably at least one of which contains oxygen, and at least one solvent in appropriate amounts to form the slurry or solution. Preferably, a solution is formed at this stage of the catalyst preparation. Generally, the metal compounds contain the elements required for the particular catalyst, as previously defined.

Suitable solvents include water, alcohols including, but not limited to, methanol, ethanol, propanol, and diols, etc., as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed at the time of mixing.

For example, when a mixed metal oxide of the formula $Mo_aV_bTe_cNb_dO_e$ is to be prepared, an aqueous solution of telluric acid, an aqueous solution of niobium oxalate and a solution or slurry of ammonium paramolybdate may be sequentially added to an aqueous solution containing a predetermined amount of ammonium metavanadate, so that the atomic ratio of the respective metal elements would be in the prescribed proportions.

Once the aqueous slurry or solution (preferably a solution) is formed, the water is removed by any suitable method, known in the art, to form a catalyst precursor. Such methods include, without limitation, vacuum drying, freeze drying, spray drying, rotary evaporation and air drying. Vacuum drying is generally performed at pressures ranging from 10 mmHg to 500 mmHg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or air drying are generally preferred.

Once obtained, the catalyst precursor is calcined. The calcination may be conducted in an oxidizing atmosphere, but it is also possible to conduct the calcination in a non-oxidizing atmosphere, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 hr$^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired mixed metal oxide.

In a preferred mode of operation, the catalyst precursor is calcined in two stages. In the first stage, the catalyst precursor is calcined in an oxidizing atmosphere (e.g., air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for from 15 minutes to 8 hours, preferably for from 1 to 3 hours. Optionally, a reducing gas, such as, for example, ammonia or hydrogen, may be added during the second stage calcination.

In a particularly preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

With calcination, a catalyst is formed having, e.g., the formula $Mo_aV_bTe_cNb_dO_e$ wherein a, b, c, d and e are the relative atomic amounts of the respective elements.

The starting materials for the above mixed metal oxide are not limited to those described above. A wide range of materials including, for example, oxides, nitrates, halides or oxyhalides, alkoxides, acetylacetonates and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

A mixed metal oxide, thus obtained, exhibits excellent catalytic activities by itself. However, the mixed metal oxide can be converted to a catalyst having higher activities by grinding.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned mixed metal oxide; the viscosity, the concentration, etc. of the solvent used in the case of wet grinding; or the optimum conditions of the grinding apparatus. However, it is preferred that grinding is conducted until the average particle size of the ground catalyst precursor would usually be at most 20 μm, more preferably at most 5 μm. Improvement in the catalytic performance may be brought about by such grinding.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

The mixed metal oxide thus obtained may be used by itself as a solid catalyst, but may be formed into a catalyst together with a suitable carrier such as silica, alumina, titania, aluminosilicate, diatomaceous earth or zirconia. Further, it may be molded into a suitable shape and particle size depending upon the scale or system of the reactor.

Alternatively, the metal components of the presently contemplated catalyst may be supported on materials such as alumina, silica, silica-alumina, zirconia, titania, etc. by conventional incipient wetness techniques. In one typical method, solutions containing the metals are contacted with the dry support such that the support is wetted; then, the resultant wetted material is dried, for example, at a temperature from room temperature to 200° C. followed by calcination as described above. In another method, metal solutions are contacted with the support, typically in volume ratios of greater than 3:1 (metal solution:support), and the solution agitated such that the metal ions are ion-exchanged onto the support. The metal containing support is then dried and calcined as detailed above.

When using two or more catalysts, they may be in the form of a physical blend of the several catalysts. Preferably, the concentration of the catalysts may be varied so that the first catalyst component will have a tendency to be concentrated at the reactor inlet while subsequent catalysts will have a tendency to be concentrated in sequential zones extending to the reactor outlet. Most preferably, the catalysts will form a layered bed, with the first catalyst component forming the layer closest to the reactor inlet and the subsequent catalysts forming sequential layers to the reactor outlet. The layers may abut one another or may be separated from one another by a layer of inert material.

The reactor is of a type suitable for the use of a fixed catalyst bed in contact with a gaseous stream of reactants. For instance, a shell and tube type of reactor may be utilized, wherein one or more tubes are packed with catalyst(s) so as to allow a reactant gas stream to be passed in one end of the tube(s) and a product stream to be withdrawn from the other end of the tube(s). The tube(s) being disposed in a shell so that a heat transfer medium may be circulated about the tube(s).

In the case of the utilization of a single catalyst, the gas stream comprising the alkane, molecular oxygen and alcohol may all be fed into the front end(s) of the tube(s) together. Alternatively, the alkane and the molecular oxygen-containing gas may be fed into the front end(s) of the tube(s) while the alcohol may be fed into the tube(s) at a predetermined downstream location (typically chosen so as to have a certain minimum concentration of product alkene present in the gas stream passing through the tube(s), e.g., 3%, preferably 5%, most preferably 7%).

In the case of the utilization of two or more catalysts, e.g., a first catalyst component and a second catalyst component as described above, once again the gas stream comprising the alkane, the oxygen-containing gas and the alcohol may all be fed to the front end(s) of the tube(s) together. Alternatively, and preferably, the alkane and the molecular oxygen-containing gas may be fed into the front end(s) of the tube(s) while the alcohol may be fed into the tube(s) at a predetermined downstream location (typically chosen so at have a certain minimum concentration of product alkene present in the gas stream passing through the tube(s),as set forth above; or in the case of the utilization of layered beds of catalyst, as described above, intermediate two layered catalyst beds).

Typical reaction conditions for the oxidation of propane or isobutane to acrylic acid esters or methacrylic acid esters which may be utilized in the practice of the present invention include: reaction temperatures which can vary from 300° C. to 1000° C., but are usually in the range of from 600° C. to 1000° C.; the average contact time with the catalyst (i.e. the reactor residence time) is not more than 100 milliseconds, preferably not more than 80 milliseconds, most preferably not more than 50 milliseconds; the pressure in the reaction zone usually ranges from 0 to 75 psig, but is preferably no more than 50 psig.

EXAMPLES

Example 1

Prepare a saturated salt solution of 0.2377 g of $SnCl_4 \cdot 5H_2O$ (Aldrich #244678, lot # ci13817ci, Certificate of Analysis: 37 wt % Sn, MW=350.58) in 21.0081 g of an 8 wt % solution of $H_2PtCl_6$ in water (Aldrich #262587, lot # ds14224mq, Certificate of analysis: 3.8-4 wt % Pt, MW=409.82).

Weigh

α-$Al_2O_3$ monoliths to obtain a pre-load (tare) weight. Soak monoliths in solution as specified in Table 1, below. Remove monoliths from solution, record wet soak weight, and place them in crucibles for drying under $N_2$@100° C. as specified in Table 1, below. Re-weigh monoliths and record dried weight. Decompose salts under $N_2$@250° C. for 4 hours and record weight without salts, as shown in Table 2. Cover crucibles and calcine under a 5 standard cubic foot per hour stream of dried house air by raising the temperature from ambient to 600° C., at 10° C./min, holding at 600° C. for 1 hour and then allow to cool down, and record calcined weight, as shown in Table 2. Determine weight of mixed metal oxide (MMO) loaded on monolith as shown in Table 2.

Analyze for metal loading by XRF after calcinations, as shown in Table 3.

TABLE 1

| Monolith I.D. | Tare Wt. (g) | Soaking Time (hrs) | Soak Wt.[1] (g) | Drying Time (hrs) | Dried Wt. (g) |
|---|---|---|---|---|---|
| A | 1.9404 | 1.5 | 3.8062 | 1 | 2.1164 |
| B | 1.5050 | 1.5 | 3.4118 | 1 | 1.6805 |
| C | 1.6494 | 4 | 3.4082[2] | 16 | 1.7883 |
| D | 2.0952 | 16 | 3.8435[3] | 1 | 2.4625 |

[1]Soak Wt.-obtained by weighing wet monoliths after allowing time for residual solution to drip off.
[2]Use left-over solution after soaking B.
[3]Use left-over solution after soaking A.

TABLE 2

| Monolith I.D. | Weight w/o Salts (g) | Calcined Weight (g) | Weight of MMO (g) |
|---|---|---|---|
| A | 2.0593 | 2.0123 | 0.0719 |
| B | 1.6248 | 1.5774 | 0.0724 |
| C | 1.7883 | 1.7066 | 0.0572 |
| D | 2.3583 | 2.2465 | 0.1513 |

TABLE 3

| Monolith I.D. | Actual Wt % Metal Loaded After Calcination | | |
|---|---|---|---|
| | Pt | Sn | Al |
| Blank | 0 | 0 | 18.956 |
| A | 8.3 | 0.075 | 2 |
| B | 4.7 | 0.058 | 4 |
| C | 1.401 | 0.158 | 7.808 |
| D | 5.524 | 0.576 | 6.412 |

Example 2

Procedure A

A platinum/rhodium 80 mesh screen was used as a support for preparation of a Pt/Rh/Sn(oxides) catalyst. The support (Johnson Matthey) is made of 90% platinum and 10% rhodium and it consists of 11 ply 0.003 inch diameter wire. The support was immersed in a saturated solution of $SnCl_2$ in 25% aqua regia (3:1 by volume of conc. HCl and $HNO_3$) for 30 minutes at ambient temperature. The treated gauze was then heated for 1 hour at 540° C. resulting in a loading of 0.45% Sn (and/or tin oxides) on the Pt/Rh surface.

Procedure B

Pt/Rh screen with the above-noted characteristics was first treated with aqua regia for 10 minutes at 40° C. The support was then washed with water and dried at 120° C. for 30 minutes. The surface preparation step resulted in a 1.8% by weight loss of Pt/Rh metals. The treated catalyst was immersed in a 30% tetrahydrofuran solution of triphenyltin chloride (Aldrich) for 24 hours followed by heating at 450° C. for 2 hours. This procedure generated 0.215% loading of Sn (and/or oxides).

Higher percentages of Sn (and/or oxides) can be obtained by either prolonging the treatment with aqua regia (gaining larger surface area) followed by the loading procedure described above, or by repeating the immersing/heating step until the desired loading is obtained.

What is claimed is:

1. A process for the production of esters of unsaturated carboxylic acids, said process comprising:
    passing a gaseous alkane, molecular oxygen and a gaseous alcohol to a reactor, said reactor containing one or more oxidation catalysts cumulatively effective for the oxidation of said alkane to an ester of its corresponding unsaturated carboxylic acid with said alcohol;
    said reactor being operated at a temperature of from 500° C. to 1000° C., with a reactor residence time no greater than 100 milliseconds.

2. The process according to claim 1, wherein said one or more oxidation catalysts cumulatively effective for the oxidation of said alkane to an ester of its corresponding unsaturated carboxylic acid with said alcohol comprises a mixed metal oxide having the empirical formula $$Mo_aV_bM_cN_dQ_eX_fO_g$$

wherein
M is an element selected from the group consisting of Te and Sb,
N is at least one element selected from the group consisting of Nb, Ta, W, Ti, Al, Zr, Cr, Mn, B, In, As, Ge, Sn, Li, Na, K, Rb, Cs, Fr, Be, Mg, Ca, Sr, Ba, Hf and P,
Q is at least one element selected from Group 8 of the periodic table of the elements,
X is at least one element selected from the group consisting of Pb and Bi, a, b, c, d, e, f and g represent relative atomic amounts of the elements, and when a=1, b=0.01 to 1.0, c=0.01 to 1.0, d=0.01 to 1.0, e=0.001 to 0.1, f=0.001 to 0.1 and g depends on the oxidation state of the elements other than oxygen.

3. A process for the production of esters of unsaturated carboxylic acids, said process comprising:
passing a first gaseous stream comprising an alkane and molecular oxygen to a reactor;
passing a second gaseous stream comprising an alcohol to said reactor;
said reactor containing one or more oxidation catalysts cumulatively effective for the oxidation of said alkane to an ester of its corresponding unsaturated carboxylic acid with said alcohol;
said one or more oxidation catalysts comprising a first catalyst effective for the oxidation of said alkane to its corresponding alkene and a second catalyst effective for the oxidation of said alkene, in the presence of said alcohol, to an ester of its corresponding unsaturated carboxylic acid with said alcohol;
said first catalyst being disposed in a first reaction zone;
said second catalyst being disposed in a second reaction zone;
said first reaction zone being disposed upstream of said second reaction zone relative to a direction of flow of said first gaseous stream through said reactor;
said second gaseous stream being fed to said reactor intermediate said first reaction zone and said second reaction zone;
said first reaction zone being operated at a temperature of from 500° C. to 1000° C., with a first reaction zone residence time of no greater than 100 milliseconds;
said second reaction zone being operated at a temperature of from 100° C. to 300° C., with a second reaction zone residence time of no greater than 100 milliseconds.

4. The process according to claim 3, wherein said first catalyst effective for the oxidation of said alkane to its corresponding alkene comprises a reducible metal oxide promoted with a metal selected from Group 8 of the periodic table of the elements supported on a three-dimensional support structure.

5. The process according to claim 4, wherein said Group 8 promoter metal is selected from the group consisting of Pt, Pd, Rh, Ir, Ru and mixtures thereof.

6. The process according to claim 4, wherein said reducible metal oxide is an oxide of a metal selected from the group consisting of Cu, Cr, V, Mn, Nb, Mo, W, Re, Ga, Ge, In, Sn, Sb, Tl, Pb, Bi, Te, As, Se, Zn, Y, Zr, Ta, Ce, Pr, Nd, Pm, Sm, Eu, Gd, Tb, Dy, Ho, Er, Tm, Yb, Lu and mixtures thereof.

7. The process according to claim 3, wherein said first catalyst effective for the oxidation of said alkane to its corresponding alkene comprises platinum and tin supported on a three-dimensional structure.

8. The process according to claim 3, wherein said first catalyst effective for the oxidation of said alkane to its corresponding alkene comprises platinum, rhodium and tin and/or tin oxides.

9. The process according to claim 3, wherein said second catalyst effective for the oxidation of said alkene, in the presence of said alcohol, to an ester of its corresponding unsaturated carboxylic acid with said alcohol is selected from the group consisting of:
(A) a catalyst comprising a mixed metal oxide having the empirical formula $$Mo_aV_bM_cN_dO_e$$

wherein
M is selected from the group consisting of Te and Sb,
N is at least one element selected from the group consisting of Nb, Ta, W, Ti, Al, Zr, Cr, Mn, B, In, As, Ge, Sn, Li, Na, K, Rb, Cs, Fr, Be, Mg, Ca, Sr, Ba, Hf and P,
a, b, c, d and e represent relative atomic amounts of the elements, and
when a=1, b=0.01 to 1.0, c=0.01 to 1.0, d=0.01 to 1.0 and e depends on the oxidation state of the elements other than oxygen;
(B) a catalyst comprising a mixed metal oxide having the empirical formula $$Mo_aSb_bO_c$$

wherein
a, b and c represent relative atomic amounts of the elements, and
when a=1, b=0.01 to 1.0, and c depends on the oxidation state of the elements other than oxygen; and
(C) a catalyst comprising a mixed metal oxide having the empirical formula $$Mo_aSb_bBi_cO_d$$

wherein
a, b, c and d represent relative atomic amounts of the elements, and
when a=1, b=0.01 to 1.0, c=0.01 to 1.0 and d depends on the oxidation state of the elements other than oxygen.

10. The process according to claim 3, wherein said second catalyst effective for the oxidation of said alkene, in the presence of said alcohol, to an ester of its corresponding unsaturated carboxylic acid with said alcohol is selected from the group consisting of:
(a) a supported catalyst comprising at least one element selected from the group consisting of elements of Groups 5B, 6B, 7B and 8 of the periodic table of the elements promoted with at least one element selected from Group 1B of the periodic table of the elements plus bismuth oxide acetate;
(b) a catalyst comprising ruthenium;
(c) catalyst comprising Pd and Bi on a support;
(d) a supported catalyst comprising Pd and at least one element selected from the group consisting of elements of Groups 3A, 4A, 5A and 6B of the periodic table of the elements and at least one element selected from the group consisting of elements of Groups 3B and 4B of the periodic table of the elements;
(e) a supported catalyst comprising Pd and at least one element of Group 1B of the periodic table of the elements;
(f) a supported catalyst comprising Pd an Pb; and (g) a supported catalyst comprising Pd and at least one element selected from the group consisting of Ba, Au, La, Nb, Ce, Zn, Pb, Ca, Sb, K, Cd, V and Te.

11. A process for the production of esters of unsaturated carboxylic acids, said process comprising:

passing a first gaseous stream comprising an alkane and molecular oxygen to a reactor;

passing a second gaseous stream comprising an alcohol to said reactor;

said reactor containing one or more oxidation catalysts cumulatively effective for the oxidation of said alkane to an ester of its corresponding unsaturated carboxylic acid with said alcohol;

said one or more oxidation catalysts comprising a first catalyst effective for the oxidation of said alkane to its corresponding unsaturated aldehyde and a second oxidation catalyst effective for the oxidation of said unsaturated aldehyde, in the presence of said alcohol, to an ester of its corresponding unsaturated carboxylic acid with said alcohol;

said first catalyst being disposed in a first reaction zone;

said second catalyst being disposed in a second reaction zone;

said first reaction zone being disposed upstream of said second reaction zone relative to a direction of flow of said first gaseous stream through said reactor;

said second gaseous stream being fed to said reactor intermediate said first reaction zone and said second reaction zone;

said first reaction zone being operated at a temperature of from 500° C. to 1000° C., with a first reaction zone residence time of no greater than 100 milliseconds;

said second reaction zone being operated at a temperature of from 100° C. to 300° C., with a second reaction zone residence time of no greater than 100 milliseconds.

12. A process for the production of esters of unsaturated carboxylic acids, said process comprising:

passing a first gaseous stream comprising an alkane and molecular oxygen to a reactor;

passing a second gaseous stream comprising an alcohol to said reactor;

said reactor containing one or more oxidation catalysts cumulatively effective for the oxidation of said alkane to an ester of its corresponding unsaturated carboxylic acid with said alcohol;

said one or more oxidation catalysts comprising a first catalyst effective for the oxidation of said alkane to its corresponding alkene, a second catalyst effective for the oxidation of said alkene to its corresponding unsaturated aldehyde, and a third catalyst effective for the oxidation of said unsaturated aldehyde, in the presence of said alcohol, to an ester of its corresponding unsaturated carboxylic acid with said alcohol;

said first catalyst being disposed in a first reaction zone;

said second catalyst being disposed in a second reaction zone;

said third catalyst being disposed in a third reaction zone;

said first reaction zone being disposed upstream of said second reaction zone relative to a direction of flow of said first gaseous stream through said reactor;

said second reaction zone being disposed upstream of said third reaction zone relative to said direction of flow of said first gaseous stream through said reactor;

said second gaseous stream being fed to said reactor intermediate said second reaction zone and said third reaction zone;

said first reaction zone being operated at a temperature of from 500° C. to 1000° C., with a first reaction zone residence time of no greater than 100 milliseconds;

said second reaction zone being operated at a temperature of from 200° C. to 400° C., with a second reaction zone residence time of no greater than 100 milliseconds;

said third reaction zone being operated at a temperature of from 100° C. to 300° C., with a third reaction zone residence time of no greater than 100 milliseconds.

\* \* \* \* \*